(12) United States Patent
Lan et al.

(10) Patent No.: US 11,460,174 B2
(45) Date of Patent: Oct. 4, 2022

(54) LAMP BRACKET AND BRACKET-TYPE UV LAMP

(71) Applicant: SHENZHEN GUANKE TECHNOLOGIES CO., LTD, Shenzhen (CN)

(72) Inventors: Qing Lan, Shenzhen (CN); Ligen Liu, Shenzhen (CN); Shoubao Chen, Shenzhen (CN); Tianlong Dai, Shenzhen (CN)

(73) Assignee: SHENZHEN GUANKE TECHNOLOGIES CO., LTD, Shenzhen (CN)

( * ) Notice: Subject to any disclaimer, the term of this patent is extended or adjusted under 35 U.S.C. 154(b) by 233 days.

(21) Appl. No.: 16/898,716

(22) Filed: Jun. 11, 2020

(65) Prior Publication Data

US 2021/0356102 A1 Nov. 18, 2021

(30) Foreign Application Priority Data

May 13, 2020 (CN) .......................... 202020797194.3

(51) Int. Cl.
| | |
|---|---|
| *F21V 19/00* | (2006.01) |
| *F21V 17/00* | (2006.01) |
| *A61L 9/20* | (2006.01) |
| *G01J 5/22* | (2006.01) |
| *F21Y 103/00* | (2016.01) |

(52) U.S. Cl.
CPC .............. *F21V 19/008* (2013.01); *A61L 9/20* (2013.01); *F21V 17/00* (2013.01); *G01J 5/22* (2013.01); *A61L 2209/12* (2013.01); *F21Y 2103/00* (2013.01)

(58) Field of Classification Search
CPC . A61L 2/10; A61L 9/20; F21V 19/008; F21V 23/0442; F21V 23/0471–0485; H01R 33/05–465
See application file for complete search history.

(56) References Cited

U.S. PATENT DOCUMENTS 9,603,959 B2 * 3/2017 Zulyniak .................... A61L 2/10

FOREIGN PATENT DOCUMENTS

| CN | 201715306 U | * | 1/2011 |
| CN | 201827673 U | * | 5/2011 |
| CN | 201897111 U | * | 7/2011 |
| CN | 107676643 A | * | 2/2018 |

* cited by examiner

*Primary Examiner* — Mariceli Santiago
(74) *Attorney, Agent, or Firm* — Maier & Maier, PLLC (57) ABSTRACT

A lamp bracket and bracket-type UV fluorescent lamp. The lamp bracket includes: a backboard component, the first lamp base component, the second lamp base component and an inductive component; the first lamp base component is provided on one end of the backboard component; the second lamp base component is provided on the other end of the backboard component, connects to the first lamp base component electrically and is provided with a mounting groove, and works with the first lamp base component and backboard component to form a containing groove in an enclosure way which is used for installing UV fluorescent tube; inductive component is provided in the mounting groove, connects to the second lamp base component and/or the first lamp base component electrically, is used for sensing humans, works with the second lamp base component and/or the first lamp base component to turn on or turn off the fluorescent tube.

19 Claims, 6 Drawing Sheets

LAMP BRACKET AND BRACKET-TYPE UV LAMP

CROSS-REFERENCE TO RELATED APPLICATIONS

This application claims the priority of Chinese Patent Application No. 2020207971943 filed on May 13, 2020, the disclosure of which is incorporated herein by reference.

FIELD

The embodiments relate to the technical field of lighting equipment, particularly to a lamp bracket and a bracket-type UV fluorescent lamp using the lamp bracket.

BACKGROUND

In daily work and life, poor indoor ventilation is likely to breed bacteria, which does harm to people's health. UV fluorescence can be used for sterilization and disinfection indoors. For example, after cleaning classrooms, UV fluorescence can be applied to sterilize classrooms. Ultraviolet rays do harm to people's eyes and skin, so when UV fluorescence is applied, it should be ensured that there are no people indoors; however, the UV fluorescent lamp may be turned on by mistake, and users may stay in an environment where there is UV fluorescence for a long time without consciousness, and finally the users' eyes and skin will be damaged.

The foregoing content is only used for assisting in understanding the technical scheme of the invention, but not mean the acknowledgement of that the above content is a prior art.

SUMMARY

A purpose is to provide a lamp bracket to enhance the safety of UV fluorescent tube in use.

To realize the above purpose, the lamp bracket is used for installing the UV fluorescent tube, the lamp bracket includes:

a backboard component;

the first lamp base component provided on one end of the backboard component;

the second lamp base component provided one the other end of the backboard component, connecting to the first lamp base component, provided with a mounting groove for installing the UV fluorescent tube, working with the first lamp base component and the backboard component to form the containing groove in an enclosure way; and inductive component provided in the mounting groove, connecting to the second lamp base component and/or the first lamp base component, used for sensing human bodies, working with the second lamp base component and/or the first lamp base component to turn on or turn off the UV fluorescent tube.

In one embodiment, the mounting groove and the containing groove are provided in the same direction;

and/or, the inner wall of the containing groove is provided in a cambered shape.

In one embodiment, the inductive component comprises:

circuit board provided in the mounting groove and connecting to the second lamp base component and/or the first lamp base component electrically; and IR sensor provided on the circuit board and at least partially exposing to the notch of the mounting groove.

In one embodiment, the lamp bracket also comprises a cover plate provided on the second lamp base component in a dismountable way, the cover plate covers the notch of the mounting groove, and the cover plate is provided with offsetting holes corresponding to the IR sensor.

In one embodiment, the inductive component also comprises a microwave sensor provided on the circuit board, the microwave sensor and the IR sensor are provided at intervals, and the microwave sensor's microwave receiving & sending end is provided just facing the notch of the mounting groove.

In one embodiment, the lamp bracket also comprises a net shield whose both ends connect to the first lamp base component and the second lamp base component respectively to make the net shield cover the containing groove, and the net shield is provided with several light holes connecting to the containing groove.

In one embodiment, the first lamp base component comprises the first base and the first end cover connecting to the backboard component, the first base and/or the first end cover are/is provided with the first avoiding hole, the first base and the first end cover connect, and the first avoiding hole passes through both sides of the first base and/or the first end cover;

the second lamp base component comprises the second base and the second end cover connecting to the backboard component, the second base and the second end cover connect to form the mounting groove and two locating cavities in an enclosure way, two the locating cavities and the mounting grooves are provided at intervals, the second base and/or the second end cover are provided with two second avoiding hole, and one the second avoiding hole connects to one the locating cavity;

the net shield comprises a shield body, the first connection part and two second connection parts, the shield body's one end connects to the first connection part, the other end of the shield body connects to two the second connection parts, and two the second connection parts are provided at intervals;

the first connection part passes through the first avoiding hole, one the second connection part goes through one the second avoiding hole and is partially contained in two the locating cavities, the shield body covers the containing groove, and the shield body is provided with several the light holes.

In one embodiment, the second connection part comprises a connecting arm and convex part connecting to the shield body, the convex part is provided on one end of the connecting arm away from the shield body and is on one surface of the connecting arm facing the second lamp base component;

the convex part goes through the second avoiding hole and is included in the locating cavity.

In one embodiment, the lamp bracket also comprises a clamping part provided on one surface of the backboard component facing the net shield and connecting to the periphery of any of the light holes;

and/or, the lamp bracket comprises a bracket installation clamp is snap-fitted with the surface of the backboard component back on to the containing groove, and the bracket installation clamp is used for connecting a wall.

In one embodiment, the surface of the second lamp base component facing the mounting groove is provided with a protruding shielding metal plate which separates the mounting groove into the first slot and the second slot;

the lamp bracket also comprises a control circuit connecting to the inductive component electrically, the inductive component is provided in the first slot, and the control circuit is provided in the second slot.

An embodiment also provides a bracket-type UV fluorescent lamp comprising at least one UV fluorescent tube and the lamp bracket; the UV fluorescent tube is provided in the mounting groove of the lamp bracket and connects to the first lamp base component and the second lamp base component electrically.

A solution includes a backboard component whose both ends connect the first lamp base component and the second lamp base component respectively, the backboard component, the first lamp base component and the second lamp base component work together to form a containing groove in an enclosure way, and the second lamp base component is provided with a mounting groove; and, at least one UV fluorescent tube is provided in the containing groove, connects to the first lamp base component and the second lamp base component electrically, so that the first lamp base component and/or the second lamp base component can provide power for the UV fluorescent tube to make the UV fluorescent tube on; in another aspect, the inductive component is provided in the mounting groove, connects to the second lamp base component and/or the first lamp base component electrically, when the inductive component senses that there are people in the environment, the inductive component can send impulse signals to the second lamp base component and/or the first lamp base component, after the second lamp base component and/or the first lamp base component receive/s the inductive component's pulse signals regarding that there are people in the environment, the second lamp base component and/or the first lamp base component will stop supplying power for the UV fluorescent tube, and then the UV fluorescent tube will be off, protecting skin and/or eyes from damage of ultraviolet rays; when the inductive component senses that there are no people in the environment, the second lamp base component and/or the first lamp base component will supply power for the UV fluorescent tube normally to make the UV fluorescent tube on. in another aspect, the first lamp base component and the second lamp base component are provided on both ends of the backboard component to form an integral bracket-type structure, simplify the structure of the lamp bracket, reduce the manufacturing cost, facilitate installation of the backboard component, the first lamp base component and the second lamp base component to a wall as a whole and improve the convenience of installing the lamp bracket. In yet another aspect, the first lamp base component and the second lamp base component can be provided with a corresponding amount of installation positions with which one or several UV fluorescent tubes can be installed to facilitate users to adjust the sterilization strength as needed. The lamp bracket according to this utility model is used for installing the UV fluorescent tube to improve the safety of UV sterilization and disinfection.

BRIEF DESCRIPTION OF THE DRAWINGS

To better describe the technical schemes, a brief introduction of drawings to be used in the descriptions of the embodiment or prior art is made hereby. Obviously, the drawings described below are only several embodiments. For common technicians in this field, they can obtain other drawings based on these structures shown in the drawings without making additional creative endeavors.

The implementation, functional characteristics and advantages of the utility model will be further illustrated hereinafter in conjunction with the embodiments and accompanying drawings.

DETAILED DESCRIPTION

A clear and complete description of the technical schemes combined with the drawings in embodiments, the embodiments clearly and completely describe the technical programs. Obviously, only some embodiments (instead of all the utility model embodiments) are described here. Based on the embodiment, all other embodiments acquired by the common technicians in this field without creative work, shall be in the protection scope of this utility model.

It should be noted that, if there is a directional indication (upper, lower, left, right, front, and rear, etc.) in the embodiment, the directional indication is only used to explain the relative positional relationship, motion condition, etc. between the components in a particular position (as shown in the drawing), and if the particular attitude is changed, the directional indication is changed accordingly.

In addition, if there are descriptions relating to "first", "second" and the like in embodiments of the utility model, such descriptions of "first", "second" and the like are for descriptive purposes only and are not to be construed as indicating or implying their relative importance or implying an indication of the number of indicated technical features. As such, a feature that defines as "first", "second" may explicitly or implicitly include at least one of that features. In addition, the "and/or" as stated in the whole text should be understood as there are three paralleled schemes where scheme A, or scheme B or scheme A and scheme B can be met at the same time (taking "A and/or B as an example"). In addition, the technical schemes of embodiments may be combined with each other, but must be available for common technicians in this field, and when the combination of the technical scheme is contradictory or impossible, it should be considered that the combination of the technical scheme does not exist and not fall within the scope of the utility model.

Figure 1:
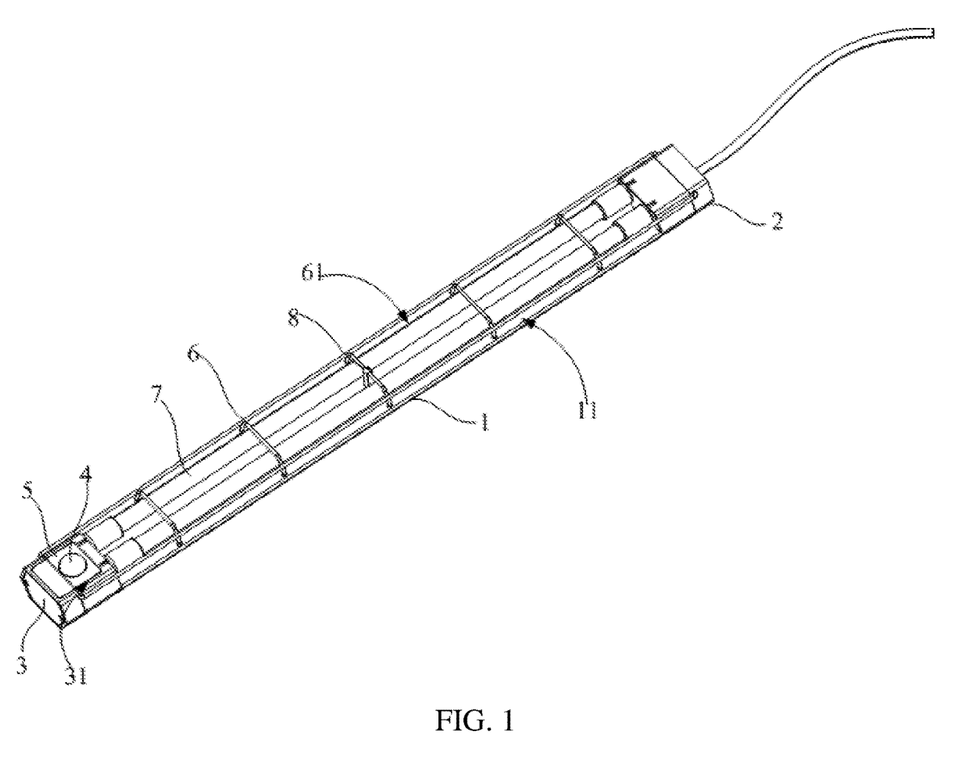
FIG. 1 is a schematic diagram showing the structure of an embodiment of lamp bracket.
Figure 2:
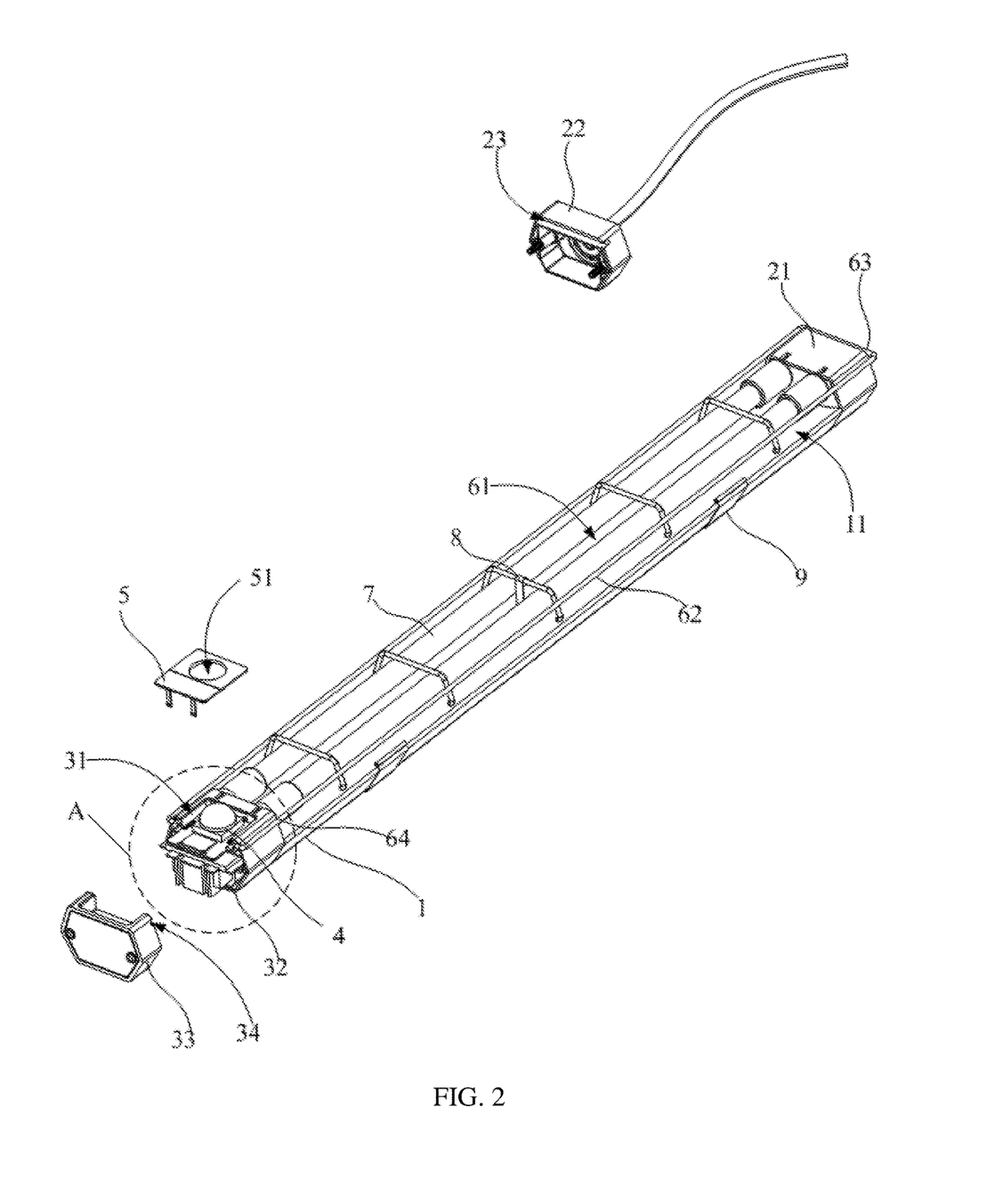
FIG. 2 is a schematic diagram showing the assembly structure of lamp bracket in FIG. 1.
Figure 3:
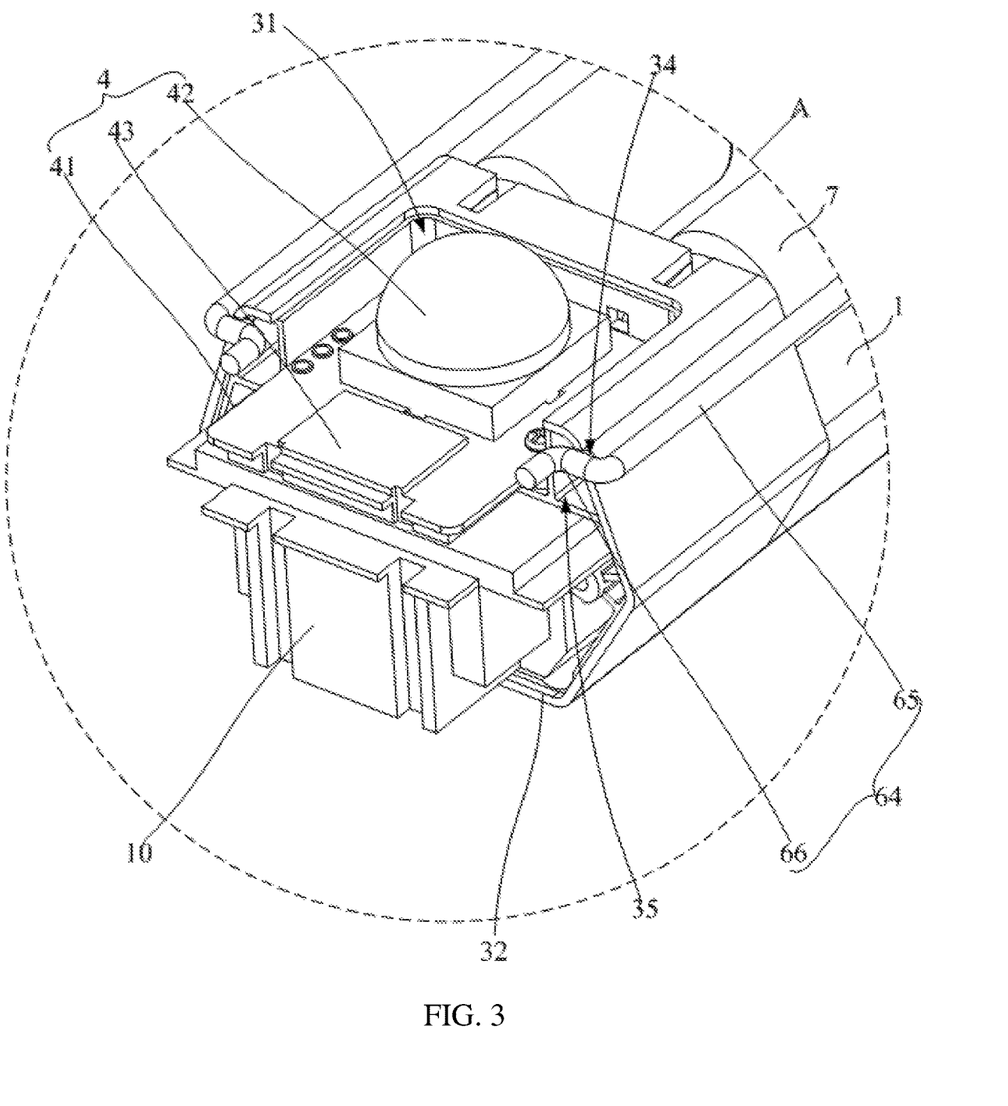
FIG. 3 is a partial enlarged drawing of section A in FIG. 2.
Figure 4:
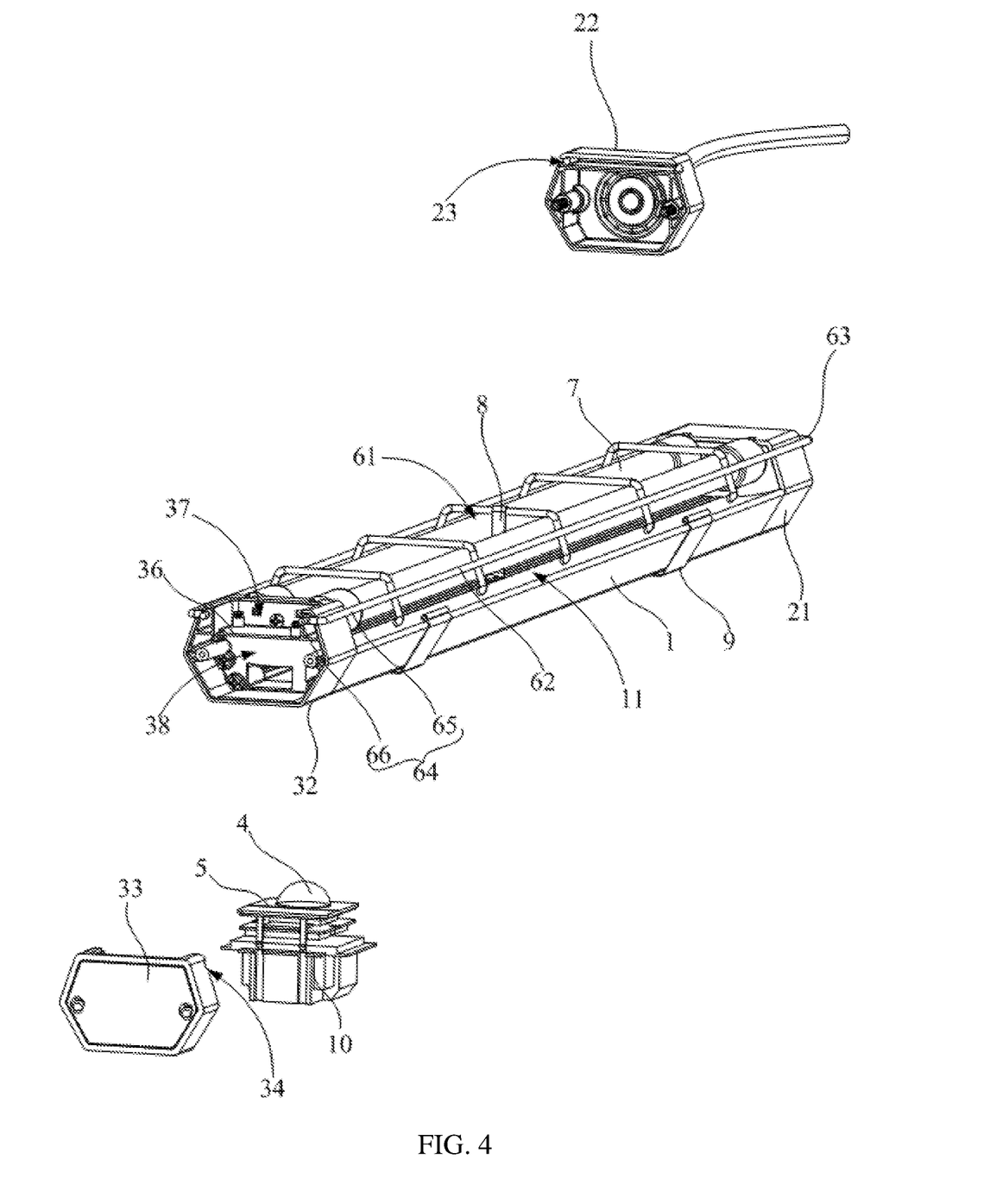
FIG. 4 is a schematic diagram showing the assembly structure of the lamp bracket in FIG. 2 from another perspective.
Figure 5:
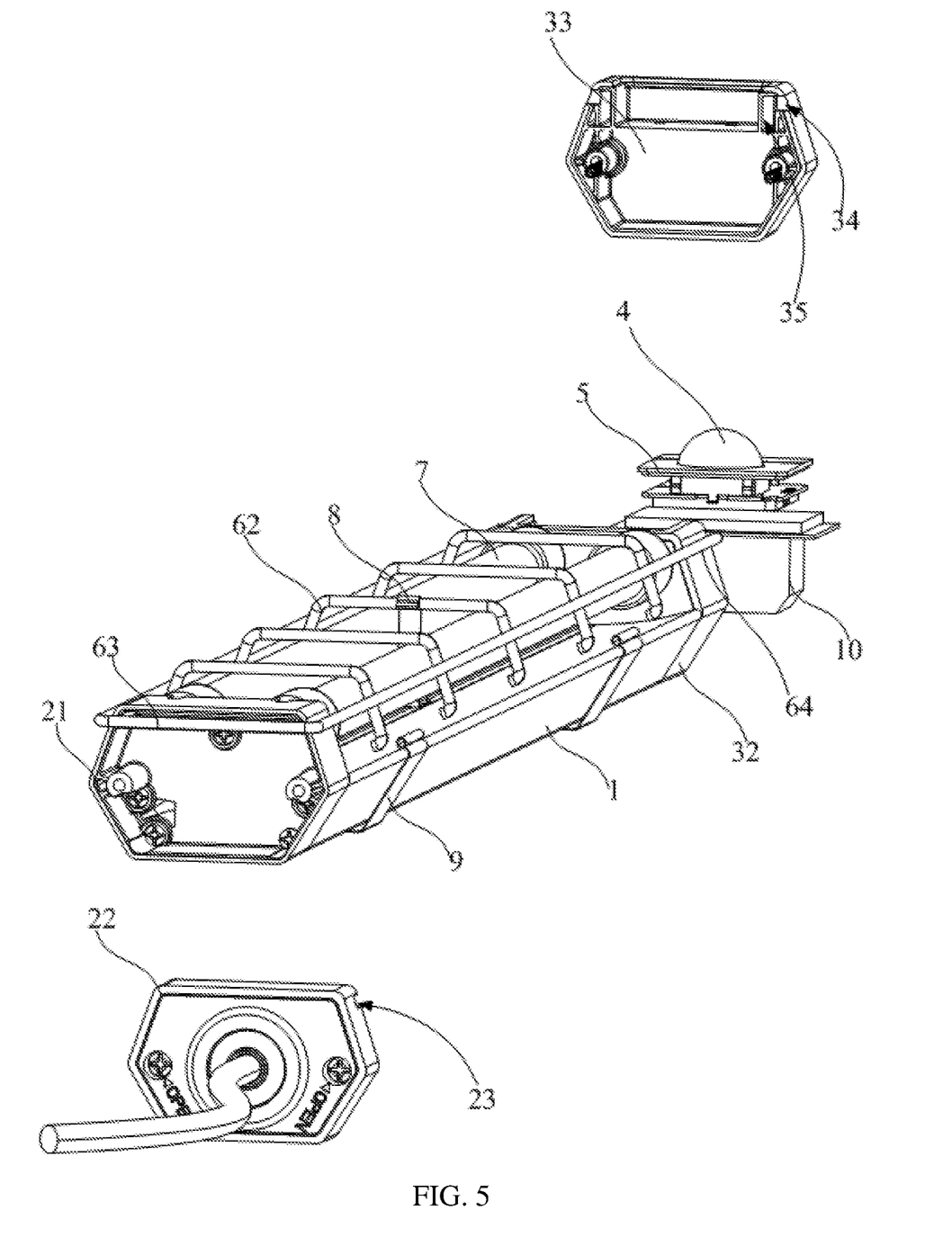
FIG. 5 is a schematic diagram showing the assembly structure of the lamp bracket in FIG. 2 from another perspective.
Figure 6:
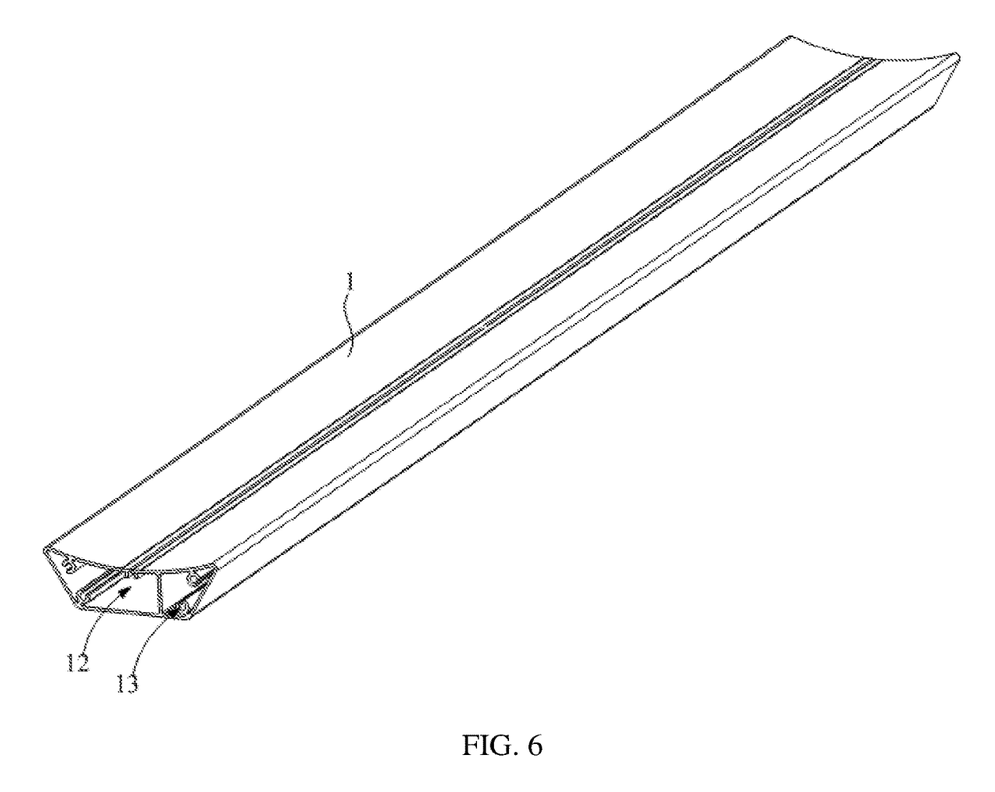
FIG. 6 is a schematic diagram showing the structure of the backboard component in FIG. 2.

This utility model provides a lamp bracket used for installing the UV fluorescent tube to make the UV fluorescent tube send ultraviolet rays and realize environment sterilization and disinfection. Refer to FIG. 1, it is a schematic diagram showing the structure of an embodiment of lamp bracket of this utility model; Refer to FIG. 2, it is a schematic diagram showing the assembly structure of the lamp bracket in FIG. 1; Refer to FIG. 3, it is a partial enlarged drawing of section A in FIG. 2; Refer to FIG. 4, it is a schematic diagram showing the assembly structure of the lamp bracket in FIG. 2 from another perspective; Refer to FIG. 5, it is a schematic diagram showing the assembly structure of the lamp bracket in FIG. 2 from another perspective; Refer to FIG. 6, it is a schematic diagram showing the structure of the backboard component in FIG. 2.

In the Embodiment of the utility model, as shown in FIG. 1 and according to FIG. 2 and FIG. 3, the lamp bracket includes: backboard component 1, the first lamp base component 2, the second lamp base component 3 and inductive component 4; the first lamp base component 2 is provided on one end of the backboard component 1; the second lamp base component 3 is provided on the other end of the backboard component 1, connects to the first lamp base component 2 electrically and is provided with a mounting groove 31, and works with the first lamp base component 2 and backboard component 1 to form a containing groove 11 in an enclosure way which is used for installing UV fluorescent tube 7; that is, the second lamp base component 3 and the first lamp base component 2 are face to face and are provided on one surface of backboard component 1 in a protruding way, and the second lamp base component 3 and the first lamp base component 2 connect to both ends of UV fluorescent tube 7 respectively; inductive component 4 is provided in the mounting groove 31, connects to the second lamp base component 3 and/or the first lamp base component 2 electrically, is used for sensing human bodies, works with the second lamp base component 3 and/or the first lamp base component 2 to turn on or turn off the UV fluorescent tube 7.

Wherein, inductive component 4 can be IR sensor 42 and/or microwave sensor 43.

In practical application of this embodiment, inductive component 4 can be a circuit structure provided with a micro-control unit, inductive component 4 connects to the first lamp base component 2 and the second lamp base component 3, inductive component 4 is used for sensing whether there are human bodies in the environment to work with the first lamp base component 2 and the second lamp base component 3 to supply power for UV fluorescent tube 7 to control turning-on or turning-off of UV fluorescent tube 7.

The technical solution of this utility model comprises a backboard component 1 whose both ends connect the first lamp base component 2 and the second lamp base component 3 respectively, the backboard component 1, the first lamp base component 2 and the second lamp base component 3 work together to form a containing groove 11 in an enclosure way, and the second lamp base component 3 is provided with a mounting groove 31; and, at least one UV fluorescent tube 7 is provided in the containing groove 11, connects to the first lamp base component 2 and the second lamp base component 3 electrically, so that the first lamp base component 2 and/or the second lamp base component 3 can provide power for the UV fluorescent tube 7 to make the UV fluorescent tube 7 on; in another aspect, inductive component 4 is provided in the mounting groove 31, connects to the second lamp base component 3 and/or the first lamp base component 2 electrically, when inductive component 4 senses that there are people in the environment, inductive component can send impulse signals to the second lamp base component 3 and/or the first lamp base component 2, after the second lamp base component 3 and/or the first lamp base component 2 receive/s pulse signals of inductive component 4 regarding that there are people in the environment, the second lamp base component 3 and/or the first lamp base component 2 will stop supplying power for UV fluorescent tube 7, and then UV fluorescent tube 7 will be off, protecting skin and/or eyes from damage of ultraviolet rays; when the inductive component 4 senses that there are no people in the environment, the second lamp base component 3 and/or the first lamp base component 2 will supply power for UV fluorescent tube 7 normally to make UV fluorescent tube 7 on. in another aspect, the first lamp base component 2 and the second lamp base component 3 are provided on both ends of the backboard component 1 to form an integral bracket-type structure, simplify the structure of the lamp bracket, reduce the manufacturing cost, facilitate installation of the backboard component 1, the first lamp base component 2 and the second lamp base component 3 to a wall as a whole and improve the convenience of installing the lamp bracket. In yet another aspect, the first lamp base component 2 and the second lamp base component 3 can be provided with a corresponding amount of installation positions with which one or several UV fluorescent tubes 7 can be installed to facilitate users to adjust the sterilization strength as needed. The lamp bracket according to this utility model is used for installing the UV fluorescent tube 7 to improve the safety of UV sterilization and disinfection.

Optionally, backboard component 1 can be a rectangular alloy plate, and the first lamp base component 2 and the second lamp base component 3 can be located at both ends of backboard component 1 via screws. Wherein, backboard component 1 can be made of aluminum alloy.

Optionally, the first lamp base component 2 and the second lamp base component 3 are provided with tube holders which can be commonly used ports for installing tubes, that is, UV fluorescent tube 7 can be inserted into the tube holder, the tube holder and UV fluorescent tube 7 connect electrically to provide power for UV fluorescent tube 7. Understandably, the tube holders on the first lamp base component 2 and the second lamp base component 3 are normal specifications to adapt to the port of the corresponding UV fluorescent tube, so that different power sizes of UV fluorescent tubes can connect to the first lamp base component 2 and the second lamp base component 3.

Optionally, the lamp bracket comprises a battery component which can be provided in backboard component 1, the first lamp base component 2 or the second lamp base component 3, and the battery component connects to the first lamp base component 2 and the second lamp base component 3 electrically.

Optionally, the lamp bracket comprises lead whose one end connects to a plug and the other end connects to the first lamp base component 2 or the second lamp base component 3. In other words, the first lamp base component 2 or the second lamp base component 3 accesses the power grid via lead.

Optionally, the lamp bracket also comprises a control circuit 10 which connects to inductive component 4 electrically, control circuit 10 works with inductive component 4 to sense human bodies so as to control power supply of UV fluorescent tube 7 for the first lamp base component 2 and the second lamp base component 3. In other words, to improve the precision of controlling illumination of UV fluorescent tube 7, a control circuit 10 relatively independent from inductive component 4 can be provided, and control circuit 10 can be a circuit structure comprising some components, like power adapter, signal transceiver, etc.

Optionally, under the premise that inductive component 4 is provided in mounting groove 31, and inductive component 4 can effective capture signals about the existence of people in the environment, it is not restricted that the opening of mounting groove 31 is provided on any side of the second lamp base component 3. In other words, opening of mounting groove 31 can be provided on one side of the second lamp base component 3 away from backboard component 1, or, the notch of mounting groove 31 and containing groove 11 are provided in the same direction.

In one embodiment of the utility model, according to FIG. 2 and FIG. 3, mounting groove 31 and containing groove 11 are provided in the same direction. In other words, the notch of mounting groove 31 and containing groove 11 are provided in the same direction; the notch of mounting groove 31 and the illumination side of UV fluorescent tube 7 on the lamp bracket are provided on one same side to make inductive component 4 effectively capture signals about existence of people in the environment just facing the lamp bracket to improve inductive component 4's sensitivity of sensing human bodies.

In one embodiment of the utility model, according to FIG. 2, FIG. 3 and FIG. 6, the inner wall of containing groove 11 is in a cambered shape. In other words, the first lamp base component 2 and the second lamp base component 3 are provided on the same surface of backboard component 1 in a protruding way, and it is defined that this same surface is an illumination surface in a cambered shape. When UV fluorescent tube 7 illuminates, the cambered surface can be used for reflecting rays of light irradiated onto backboard component 1 into the environment to improve the ultraviolet ray utilization of the lamp.

Optionally, the cambered can be concave or convex.

Optionally, backboard component 1 can be aluminum alloy of high reflection.

In one embodiment of the utility model, according to FIG. 2, FIG. 3, FIG. 4 and FIG. 5, inductive component 4 comprises circuit board 41 provided in mounting groove 31 and IR sensor 42 provided on circuit board 41, and IR sensor 42 connect to circuit board 41 electrically. Wherein, circuit board 41 also connect to the second lamp base component 3 and/or the first lamp base component 2 electrically; IR sensor 42 is provided on circuit board 41, and IR sensor 42 is exposed partially to the notch of mounting groove 31 at least.

In this embodiment, IR sensor 42 is partially exposed to the notch of mounting groove 31, which can effectively enlarge the signal capture scope of IR sensor 42 and avoid accidents caused in the case that the inner wall of mounting groove 31 blocks the identification scope.

In one embodiment of the utility model, according to FIG. 2, FIG. 3, FIG. 4 and FIG. 5, the lamp bracket also comprises cover plate 5 provided on the second lamp base component 3 in a dismountable way, cover plate 5 covers the notch of mounting groove 31, and cover plate 5 is provided with offsetting hole 51 corresponding to IR sensor 42.

In this embodiment, cover plate 5 covers the notch of mounting groove 31, cover plate 5 is provided with offsetting hole 51 corresponding to IR sensor 42 to make IR sensor 42 passes through offsetting hole 51 partially, avoiding external dust and steam enter mounting groove 31, avoiding short circuit of inductive component 4 arising from dust and steam and improving the working stability of inductive component 4; meanwhile, the design of cover plate 5 can make the inductive component be installed along the covering direction of the cover plate to simplify and separate the product's complex circuit into several independent working procedures to facilitate installation and maintenance of the sensing component, which adapts to repair and inspection of a large batch of production and improves the production efficiency.

In one embodiment of the utility model, according to FIG. 2, FIG. 3, FIG. 4 and FIG. 5, inductive component 4 also comprises microwave sensor 43 provided on circuit board 41, microwave sensor 43 and IR sensor 42 are provided at intervals, and the microwave receiving & sending end of microwave sensor 43 just faces the notch of mounting groove 31.

In this embodiment, circuit board 41 is also provided with a microwave sensor 43 which sends and receives microwaves and works with circuit board 41 to determine whether there are people in the environment to improve inductive component 4's sensitivity of sensing human bodies and improve the sensing accuracy, so as to overcome impacts of temperature on IR sensor 42 and impacts of metal environment on microwave sensors.

Understandably, based on the above content, under specific processing demands, it can be considered that the inductive component can be provided with IR sensor 42 or microwave sensor 43; or the inductive component can be provided with both IR sensor 42 and microwave sensor 43.

In one embodiment of the utility model, according to FIG. 2, FIG. 3, FIG. 4 and FIG. 5, the lamp bracket also comprises net shield 6 whose both ends connect to the first lamp base component 2 and the second lamp base component 3 respectively to make net shield 6 cover containing groove 11, and net shield 6 is provided with several light holes 61 connecting to containing groove 11.

In this embodiment, net shield 6 covers the notch of containing groove 11 to protect UV fluorescent tube 7 in containing groove 11 from collision of external articles, so as to improve the stability and safety of installing UV fluorescent tube 7 with the lamp bracket. Meanwhile, the design of net shield 6 can better protect UV fluorescent tube 7 to make UV fluorescent tube be installed in a bracket-type fluorescent lamp for packing, transportation and sales, which is a function not possessed by regular specifications of bracket-type lamps. In addition, the flat design of net shield facilitates that more fluorescent tubes can be provided in the bracket-type fluorescent lamp and the package volume is saved.

Optionally, net shield 6 can be made by a folded metal line. Or, net shield 6 can be made of several metal lines through welding. Or, net shield can be made through plastic injection molding. Under the premise that net shield 6 can protect UV fluorescent tube 7 provided in containing groove 11 from collision of external articles, the material of net shield 6 is not restricted here.

Preferably, net shield 6 can be made of several metal lines through welding. It is prohibited that net shield 6 is made of plastic, and it is prohibited that plastic net shield 6 is radiated by ultraviolet rays, which will lead to aging.

In one embodiment of the utility model, according to FIG. 2, FIG. 3, FIG. 4 and FIG. 5, the first lamp base component comprises the first base 21 and the first end cover 22 connecting to backboard component 1, the first base 21 and/or the first end cover 22 are/is provided with the first avoiding hole 23, the first base 21 and the first end cover 22 connect, the first avoiding hole 23 passes through both sides of the first base 21 and/or the first end cover 22;

the second lamp base component 3 comprises the second base 32 and the second end cover 33 connecting to backboard component 1, the second base 32 and the second end cover 33 connect to form mounting groove 31 and two locating cavities 35 in an enclosure way, two locating cavities 35 and mounting groove 31 are provided at intervals, the second base 32 and/or the second end cover 33 are provided with the second avoiding hole 34, and one the second avoiding hole 34 and one locating cavity 35 connect;

net shield 6 comprises shield body 62, the first connection part 63 and two second connection parts 64, one end of shield body 62 connects to the first connection part 63, the other end of shield body 62 connects to two second connection parts 64, and two second connection parts 64 are provided at intervals;

the first connection part 63 passes through the first avoiding hole 23, one the second connection part 64 passes through one the second avoiding hole 34 and is partially contained in two locating cavities 35, shield body 62 covers containing groove 11, and shield body 62 is provided with several light holes 61.

In this embodiment, the first base 21 and the first end cover 22 locate the first connection part 63, the second base 32 and the second end cover 33 locate the second connection part 64 to make shield body 62 cover containing groove 11. In other words, when UV fluorescent tube 7 needs to be dismounted from or mounted to the lamp bracket, users only need to unscrew the first end cover 22 and/or the second end cover 33 at the part to uncover containing groove 11, so that UV fluorescent tube 7 can be mounted or dismounted conveniently.

Understandably, when users only need to unscrew the first end cover 22 and/or the second end cover 33 at the part, net shield 6 can rotate by taking the first connection part 63 or the second connection part 64 as the rotating shaft, simplifying the assembly process of net shield 6. In other words, when it only needs to unscrew the first end cover 22 of the end, net shield 6 rotates by taking two second connection parts 64 as the rotating shaft; when it only needs to unscrew the second end cover 33 of the end, net shield 6 rotates by taking the first connection part 63 as the rotating shaft.

Optionally, the first connection part 63 is of a rod structure and the first connection part 63 passes through the first avoiding hole 23 rotationally.

Optionally, the second connection part 64 can be of a rod structure and possesses a bent structure. When net shield 6 is provided on the first lamp base component 2 and the second lamp base component 3, the bent structure of the second connection part 64 is provided in the second avoiding hole 34, and the bent structure is partially contained in locating cavity 35.

In one embodiment of the utility model, according to FIG. 2, FIG. 3, FIG. 4 and FIG. 5, the second connection part 64 comprises connecting arm 65 and convex part 66 connecting to shield body 62, convex part 66 is provided on one end of connecting arm away from shield body 62 and is on one surface of connecting arm 65 facing the second lamp base component 3; Convex part 66 passes through the second avoiding hole 34 and is contained in locating cavity 35.

In other words, two connecting arms 65 are provided on one end of shield body 62 face to face, one surface of both connecting arms 65 are provided with a convex part 66, and two convex parts 66 can be face-to-face or staggered. In other words, when shield body 62 needs to cover containing groove 11, one convex part 66 is just contained in one locating cavity 35.

In one embodiment of the utility model, convex part 66 can be a convex structure; or, convex part 66 can be a bent structure.

In one embodiment of the utility model, connecting arm 65 and convex part 66 can be an integral structure. In other words, connecting arm 65 and convex part 66 can be a structure formed by bending a metal rod, that is, one end of the metal rod connects to shield body 62, and one end of the metal rod away from shield body 62 is bent to form convex part 66 (the number of bending one end of the metal rod away from shield body 62 is not restricted), that is, convex part 66 can be a rod including several bent structures.

In one embodiment of the utility model, according to FIG. 2, FIG. 3, FIG. 4 and FIG. 5, lamp bracket also comprises at least one clamping part 8 provided on one surface of backboard component 1 facing net shield 6 and connecting to the periphery of any of light holes 61.

Understandably, clamping part 8 can be a bent metal part, clamping part 8 comprises the first metal part and the second metal part, the first metal part and the second metal part are provided to form an included angle, one end of the first metal part away from the second metal part connects to backboard component 1, and one end of the second metal part away from the first metal part connects to net shield 6.

Optionally, clamping part 8 can be locked onto backboard component 1 with screws.

Optionally, one end of the second metal part away from the first metal part can be provided with a fastening slot, and the inner wall of the fastening slot is snap-fitted with net shield 6.

In one embodiment of the utility model, according to FIG. 2, FIG. 3, FIG. 4 and FIG. 5, the lamp bracket comprises bracket installation clamp 9 which is snap-fitted with the surface of backboard component 1 back on to containing groove 11 and is used for connecting a wall.

In this embodiment, bracket installation clamp 9 can be made of metal, is provided with two elastic arms which form a clamping space in which backboard component 1 is clamped with two elastic arms. In other words, when the lamp bracket needs to be mounted to a wall or some frames, bracket installation clamp 9 can be mounted to a wall or some frames based on preselection, and elastic arms are back on to the wall or some frames to facilitate that backboard component 1 is provided in two elastic arms artificially.

In one embodiment of the utility model, according to FIG. 2, FIG. 3 and FIG. 4, the surface of the second lamp base component 3 facing mounting groove 31 is provided with protruding shielding metal plate 36 which separates mounting groove 31 into the first slot 37 and the second slot 38;

the lamp bracket also comprises control circuit 10 connecting to inductive component 4 electrically, one of control circuit 10 and inductive component 4 is provided in the first slot 37, and the other of the control circuit 10 and inductive component 4 is provided in the second slot 38.

In this embodiment, the surface of mounting groove 31 is provided with protruding shielding metal plate 36, so that control circuit 10 and inductive component 4 are provided on both sides of two shielding metal plates 36 respectively to reduce impacts of heat generated by control circuit 10 on inductive component 4. In another aspect, a structure where the first slot 37 and the second slot 38 are provided relatively independently is applied to realize better insulation of control circuit 10 and inductive component 4, separate the product's complex circuit into several independent working procedures to facilitate installation and maintenance of the sensing component, which adapts to repair and inspection of a large batch of production and improves the production efficiency; Meanwhile, mutual electromagnetic interference between control circuit 10 and inductive component 4 can be avoided, so the working stability of the lamp bracket can be improved.

In another aspect, shielding metal plate 36 can also serve as a mounting plate; control circuit 10 and circuit board 41 are provided on shielding metal plate 36, improving the mounting stability of control circuit 10.

In one embodiment of the utility model, control circuit 10 can be provided with a power adapter which can control electrical connection between control circuit 10 and the power grid via lead.

In one embodiment of the utility model, according to FIG. 6, backboard component 1 can be made of aluminum alloy profile. The middle part of backboard component 1 is provided with a connecting cavity 12. The connecting cavity 12 and containing groove 11 are provided at intervals. The inner wall of connecting cavity 12 can be provided with wire trimming slot 13. Lead connecting the first lamp base component 2 and the second lamp base component 3 can be laid in wire trimming slot 13. In some specific embodiments, electrical components can be provided in connecting cavity 12. For example, when a structure with a large control circuit 10 is applied, such a large control circuit 10 is hard to be contained in mounting groove 31, so control circuit 10 can be provided in connecting cavity 12 wholly or partially.

This utility model also provides a bracket-type UV fluorescent lamp. According to FIG. 1, this bracket-type UV fluorescent lamp comprises at least one UV fluorescent tube 7 and one lamp bracket. The specific structure of the lamp bracket can refer to the above embodiments. Since the bracket-type UV fluorescent lamp adopts all the technical solutions of all the aforesaid embodiments, at least the bracket-type UV fluorescent lamp can achieve all the beneficial effects of all the technical solutions of aforesaid embodiments, so unnecessary details will not be given here. Wherein, UV fluorescent tube 7 is provided in the mounting groove 31 of lamp bracket and connects to the first lamp base component 2 and the second lamp base component 3 electrically.

Understandably, bracket-type UV fluorescent lamp can comprise several UV fluorescent tubes 7 whose both ends electrically connect to the first lamp base component 2 and the second lamp base component 3 respectively.

The description is only the preferred embodiment of the utility model, and it is not for this reason that the patent scope of the utility model is limited. Any equivalent structural transformation made by using the description of the utility model and the drawing, or direct/indirect application in other related innovation technical fields under the inventive concept of the utility model, is included in the patent protection scope of the utility model.

What is claimed is:

1. A lamp bracket used for installing a UV tube, comprising:
   a backboard component;
   a first lamp base component provided on a first end of the backboard component;
   a second lamp base component provided on a second end of the backboard component, connecting to the first lamp base component, provided with a mounting groove for installing the UV tube, and working with the first lamp base component and the backboard component to enclose a containing groove; and
   an inductive component provided in the mounting groove, connecting to the second lamp base component and/or the first lamp base component, used for sensing human bodies, and working with the second lamp base component and/or the first lamp base component to turn on or turn off the UV tube,
   wherein the inductive component comprises:
      a circuit board provided in the mounting groove and connecting electrically to at least one of the second lamp base component and the first lamp base component,
      an IR sensor provided on the circuit board, the IR sensor at least partially protruding from a notch of the mounting groove, and
      a microwave sensor provided on the circuit board at intervals with the IR sensor, a receiving and sending end of the microwave sensor provided facing the notch of the mounting groove.

2. The lamp bracket as claimed in claim 1, wherein the mounting groove and the containing groove extend in the same direction; and/or
   wherein an inner wall of the containing groove is provided in a cambered shape.

3. The lamp bracket as claimed in claim 1, wherein the lamp bracket further comprises a cover plate detachably provided on the second lamp base component, the cover plate covers the notch of the mounting groove, and the cover plate is provided with offsetting holes corresponding to the IR sensor and the microwave sensor.

4. The lamp bracket as claimed in claim 1, wherein the lamp bracket further comprises a net shield whose both ends connect to the first lamp base component and the second lamp base component respectively so that the net shield covers the containing groove; and
   wherein the net shield is provided with several light holes connecting to the containing groove.

5. The lamp bracket of claim 4, wherein the first lamp base component comprises a first base and a first end cover, the first base is connected to the backboard component, the first base and/or the first end cover are/is provided with a first avoiding hole, the first base and the first end cover connect, and the first avoiding hole passes through both sides of the first base and/or the first end cover;
   wherein the second lamp base component comprises a second base and a second end cover, the second base is connected to the backboard component the second base and/or the second end cover are provided with two second avoiding holes, and one of the second avoiding holes connects to at least one locating cavity;
   wherein the net shield comprises a shield body, a first connection part and two second connection parts, a first end of the shield body connects to the first connection part, a second end of the shield body connects to the two second connection parts, and the two second connection parts are provided at intervals; and
   wherein the first connection part passes through the first avoiding hole, one of the two second connection parts goes through one of the second avoiding holes and is partially contained in the locating cavities, the shield body covers the containing groove, and the shield body is provided with several light holes.

6. The lamp bracket of claim 5, wherein at least one of the two second connection parts comprises a connecting arm and convex part connecting to the shield body, the convex part is provided on one end of the connecting arm away from the shield body and the convex part is on one surface of the connecting arm facing the second lamp base component; and
   wherein the convex part goes through the second avoiding holes and is included in the locating cavity.

7. The lamp bracket of claim 4, wherein the lamp bracket further comprises at least one clamping part provided on one surface of the backboard component facing the net shield and connected to a periphery of any of the light holes; and/or
   wherein the lamp bracket comprises a bracket installation clamp which is snap-fitted with a surface of the backboard component backing the containing groove, and the bracket installation clamp is used for connecting a wall.

8. The lamp bracket of claim 1, wherein a surface of the second lamp base component facing the mounting groove is provided with a protruding shielding metal plate which separates the mounting groove into a first slot and a second slot; and wherein the lamp bracket further comprises a control circuit electrically connected to the inductive component, the inductive component is provided in the first slot, and the control circuit is provided in the second slot.

9. A bracket-type UV lamp comprising the lamp bracket of claim 1 and a UV tube, wherein the UV tube is provided in the mounting groove of the lamp bracket and connects to the first lamp base component and the second lamp base component electrically.

10. A lamp bracket used for installing a UV tube, comprising:

a backboard component;
a first lamp base component provided on one end of the backboard component;
a second lamp base component provided on an other end of the backboard component, connecting to the first lamp base component, provided with a mounting groove for installing the UV tube, working with the first lamp base component and the backboard component to form a containing groove in an enclosure way; and
an inductive component provided in the mounting groove, connecting to the second lamp base component and/or the first lamp base component, used for sensing human bodies, working with the second lamp base component and/or the first lamp base component to turn on or turn off the UV tube,
wherein the lamp bracket further comprises a net shield whose both ends connect to the first lamp base component and the second lamp base component respectively so that the net shield covers the containing groove; and
wherein the net shield is provided with several light holes connecting to the containing groove.

11. The lamp bracket as claimed in claim 10, wherein the mounting groove and the containing groove extend in the same direction; and/or wherein an inner wall of the containing groove is provided in a cambered shape.

12. The lamp bracket as claimed in claim 10, wherein the inductive component comprises:

a circuit board provided in the mounting groove and connecting electrically to at least one of the second lamp base component and the first lamp base component, and
an IR sensor provided on the circuit board, the IR sensor at least partially protruding from a notch of the mounting groove.

13. The lamp bracket as claimed in claim 12, wherein the lamp bracket further comprises a cover plate detachably provided on the second lamp base component, the cover plate covers the notch of the mounting groove, and the cover plate is provided with offsetting holes corresponding to the IR sensor.

14. The lamp bracket as claimed in claim 12, wherein the inductive component further comprises a microwave sensor provided on the circuit board at intervals with the IR sensor, a receiving and sending end of the microwave sensor provided facing the notch of the mounting groove.

15. The lamp bracket of claim 10, wherein the first lamp base component comprises a first base and a first end cover, the first base is connected to the backboard component, the first base and/or the first end cover are/is provided with a first avoiding hole, the first base and the first end cover connect, and the first avoiding hole passes through both sides of the first base and/or the first end cover;

wherein the second lamp base component comprises a second base and a second end cover, the second base is connected to the backboard component, the second base and/or the second end cover are provided with two second avoiding holes, and one of the second avoiding holes connects to at least one locating cavity;
wherein the net shield comprises a shield body, a first connection part, and two second connection parts, a first end of the shield body connects to the first connection part, a second end of the shield body connects to the two second connection parts, and the two second connection parts are provided at intervals; and
wherein the first connection part passes through the first avoiding hole, one of the two second connection parts goes through one of the second avoiding holes and is partially contained in the locating cavities, the shield body covers the containing groove, and the shield body is provided with several light holes.

16. The lamp bracket of claim 15, wherein at least one of the two second connection parts comprises a connecting arm and convex part connecting to the shield body, the convex part is provided on one end of the connecting arm away from the shield body, and the convex part is on one surface of the connecting arm facing the second lamp base component; and wherein the convex part goes through the second avoiding holes and is included in the locating cavity.

17. The lamp bracket of claim 10, wherein the lamp bracket further comprises at least one clamping part provided on one surface of the backboard component facing the net shield and connected to a periphery of any of the light holes; and/or wherein the lamp bracket comprises a bracket installation clamp which is snap-fitted with a surface of the backboard component backing the containing groove, and the bracket installation clamp is used for connecting a wall.

18. The lamp bracket of claim 10, wherein a surface of the second lamp base component facing the mounting groove is provided with a protruding shielding metal plate which separates the mounting groove into a first slot and a second slot; and wherein the lamp bracket further comprises a control circuit electrically connected to the inductive component, the inductive component is provided in the first slot, and the control circuit is provided in the second slot.

19. A bracket-type UV lamp comprising the lamp bracket of claim 10 and a UV tube, wherein the UV tube is provided in the mounting groove of the lamp bracket and connects to the first lamp base component and the second lamp base component electrically.

* * * * *